United States Patent
Lu et al.

(10) Patent No.: US 9,725,417 B2
(45) Date of Patent: Aug. 8, 2017

(54) CDC42 INHIBITOR AND USES THEREOF

(71) Applicants: Qun Lu, Taicang (CN); Huchen Zhou, Taicang (CN); Yanhua Chen, Taicang (CN); Amy Friesland, Taicang (CN)

(72) Inventors: Qun Lu, Taicang (CN); Huchen Zhou, Taicang (CN); Yanhua Chen, Taicang (CN); Amy Friesland, Taicang (CN)

(*) Notice: Subject to any disclaimer, the term of this patent is extended or adjusted under 35 U.S.C. 154(b) by 0 days.

(21) Appl. No.: 14/807,386

(22) Filed: Jul. 23, 2015

(65) Prior Publication Data

US 2015/0329496 A1 Nov. 19, 2015

Related U.S. Application Data

(63) Continuation of application No. 14/087,662, filed on Nov. 22, 2013, now abandoned, which is a continuation-in-part of application No. PCT/CN2012/000708, filed on May 21, 2012.

(30) Foreign Application Priority Data

May 23, 2011 (CN) ............ 2011 1 0135073

(51) Int. Cl.
C07D 239/42 (2006.01)
C07D 239/69 (2006.01)
C07C 335/12 (2006.01)

(52) U.S. Cl.
CPC .......... C07D 239/42 (2013.01); C07C 335/12 (2013.01); C07D 239/69 (2013.01)

(58) Field of Classification Search
CPC .................... C07D 239/42; A61K 31/505
See application file for complete search history.

(56) References Cited

U.S. PATENT DOCUMENTS

2014/0179681 A1* 6/2014 Errico .............. C07D 401/12
514/212.01

FOREIGN PATENT DOCUMENTS

| CN | 201110135073.8 | 5/2011 |
| WO | WO 2011085129 A3 | 7/2011 |
| WO | WO 2012/159456 | 11/2012 |

OTHER PUBLICATIONS

J. Luo et al., 36 Cell, 823-837 (2009).*
T. Soussi 60 Cancer Research, 1777-1788 (2000).*
P. Lissoni et al, 7 Cancer Research, 397-401 (2009).*
National Cancer Institute (http://www.cancer.gov/) (Downloaded May 29, 2014).*
F. Bunz, Principles of Cancer Genetics 1-47, 1 (2008).*
P.K. Kuppen et al., 115 Histochemistry and Cell Biology, 67-72 (2001).*
D. Scheinberg et al., Management of Acute Leukemias, in 2 Cancer Principles & Practice of Oncology 2088, 2092 (V.T. DeVita, Jr. et al. eds., 7th ed., 2005).*
D. Druker et al., Chronic Myelogenous Leukema, in 2 Cancer Principles & Practice of Oncology 2121 (V.T. DeVita, Jr. et al. eds., 7th ed., 2005).*
S. O'Brien et al., Chronic Lymphoid Leukemias, in 2 Cancer Principles & Practice of Oncology 2133 (V.T. DeVita, Jr. et al. eds., 7th ed., 2005).*
S. Faderi et al., Myelodysplastic Syndromes, in 2 Cancer Principles & Practice of Oncology 2133 (V.T. DeVita, Jr. et al. eds., 7th ed., 2005).*
H.A. Fine, Neoplasms of the Central Nervous System in, 2 Cancer Principles & Practice of Oncology 1834-1887 (V.T. DeVita, Jr. et al. eds., 5th ed., 2005).*
I.V. Turko et al., Pharmacological Reviews, 619-634 (2002).*
F.A. Scappaticci et al., 99 Journal of the National Cancer Institute, 1232-1239 (2007).*
C. Ha et al., 104 The American Journal of Gastroenterology, 1445-1451 (2009).*
Y.S. Yoon et al., 9 The International Journal of Tuberculosis and Lung Disease, 1215-1219 (2005).*
H. Girouard et al., 100 Journal of Applied Physiology, 328-335, 332 (2006).*
R. S. Shah et al., 52 Biomedicine & Pharmacotherapy, 199-207 (2008).*
J.T. O'Brien et al., 2 The Lancet Neurology, 89-98 (2003).*
M. Liu et al., 128 International Journal of Cancer, 1269-1279 (2011).*
R. Ramchandran, 295, American Journal of Physiology, L363-L369 (2008).*
A. Mendoza-Naranjo et al., 120 Journal of Cell Science, 279-288 (2007).*
S. Holbert et al., 100 PNAS, 2712-2717 (2003).*
Z. Wang et al., 19 Drug Discovery Today, 145-150 (2014).*
R.D. Prasasya et al., 21 Seminars in Cancer Biology, 200-206 (2011).*
Kinase Inhibitors, Methods in Molecular Biology (B. Kuster ed., 2012).*
T.A. Denison et al., Heterogeneity of Cancers and Its Implication for Targeted Drug Delivery in, Cancer Targeted Drug Delivery an Elusive Dream, 337-362 (Y.H. Bae et al., eds., 2013).*
C.L. Neudauer et al., 8 Current Biology, 1151-1160 (1998).*
Chemotherapy of Neoplastic Diseases in, Goodman & Gilman's: The Pharmacological Basis of Therapeutics 853-908 (L.L. Brunton et al., eds., 11th ed., 2008).
CAS Indexed Compound, RN 587842-01-1, (Sep. 18, 2003).
CAS Indexed Compound, RN 649732-98-9, (Feb. 14, 2004).
CAS Indexed Compound, RN 587841-73-4, (Sep. 18, 2003).
CAS Indexed Compound, RN 649565-26-4, (Feb. 12, 2004).
CAS Indexed Compound, RN 587841-61-0, (Sep. 18, 2003).
CAS Indexed Compound, RN 642961-55-5; RN 642958-24-5, (Jan. 29, 2004).
CAS Indexed Compound, RN 590400-16-1, (Sep. 22, 2003).

* cited by examiner

*Primary Examiner* — Alexander R Pagano
(74) *Attorney, Agent, or Firm* — McDonald Hopkins LLC

(57) ABSTRACT

Compounds which inhibit the small G protein Rho GTPase cell division cycle protein Cdc42 are provided. Morphological analyzes of filopodia, western blots of Ccd42 phosphorylation, and effects on cellular wound healing and on growth cone formation all demonstrate that the described compounds are able to inhibit all tested Cdc42-mediated processes. The compounds effectively inhibit the effects of Cdc42 and effectively inhibit Cdc42-related cellular functions involving actin, such as Golgi organization and cell movement. Furthermore, the described Cdc42 inhibitor compounds may be provided as a medicament for the treatment of various conditions.

2 Claims, 4 Drawing Sheets

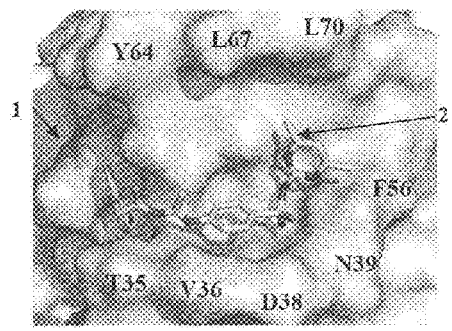
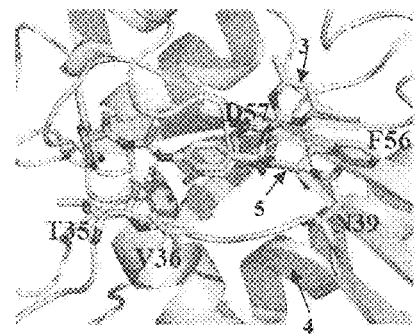
Fig 1A  Fig 1B
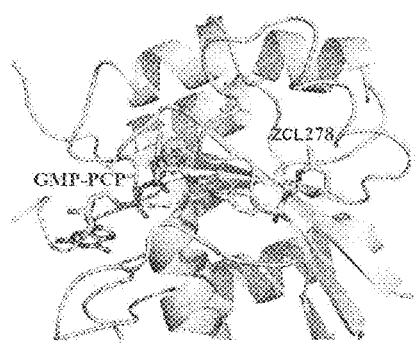
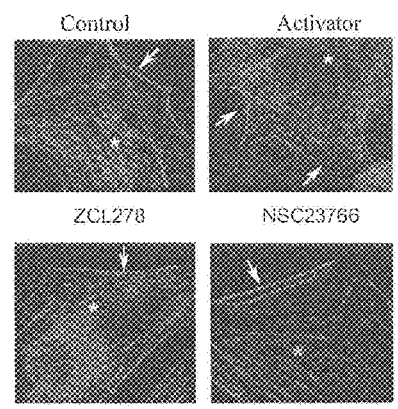
Fig 1C  Fig 2A
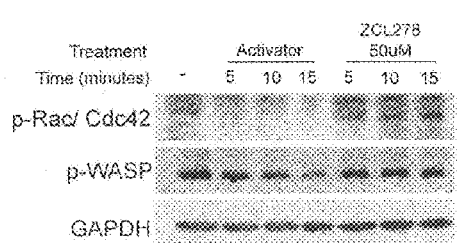
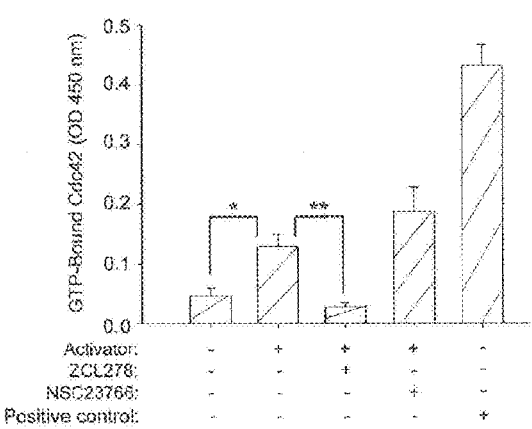
Fig 2B  Fig 2C

CDC42 INHIBITOR AND USES THEREOF

This application is a continuation of co-pending U.S. application Ser. No. 14/087,662, filed Nov. 22, 2013, which is a continuation-in-part of International Application Serial No. PCT/CN2012/000708 filed May 21, 2012, which claims priority to Chinese Application No. 201110135073.8 filed May 23, 2011, each of which is expressly incorporated by reference herein in its entirety.

TECHNICAL FIELD

The present invention relates to compounds which are inhibitors of the small G protein Rho GTPase Cdc42 and uses of the described compounds.

BACKGROUND

Cell division cycle protein Cdc42 is a sub-class of the small G protein Rho GTPase family and is an important regulatory protein of many cell biological functions. First identified in *Saccharomyces cerevisiae* for its involvement in cell polarization, Cdc42 was then recognized to play important roles in cytoskeletal reorganization, cellular endocytosis, regulation of cell cycle and cell transcription. Activation of Cdc42, like that of most GTPases, is achieved through the exchange of guanosine-5'-diphosphate (GDP) for guanosine-5'-triphsopahte (GTP) binding. Cycles of activation and inactivation of Rho family of GTPases are regulated by three important class of proteins: guanine nucleotide exchange factor (GEF), which catalyzes the release of GDP for GTP binding; GTPase activating protein (GAP) as negative regulatory factor to accelerate the hydrolysis of GTP of Rho GTPases from the active to inactive state; and Guanosine nucleotide dissociation inhibitors (GDI) to prevent the separation of GDP from Rho GTPases, thereby inhibiting Rho GTPase activity.

Recent studies reveal abnormal activity of Cdc42 widely involved in the pathophysiology of human diseases including cancer and neurodegenerative diseases. Interestingly, Cdc42 gene mutations are not found in human tumors. Its alteration is mainly reflected in its abnormal form and overexpression and is dependent on the tissue microenvironment of disorders, closely related to tumor transformation and progression. As a key regulator of neuronal morphology, Cdc42 controls the fate of normal brain development. Cdc42 knockout mice do not live to birth and show significant brain malformations. Previous studies have shown that Cdc42 activates the epithelial to mesenchymal cell transition (EMT), playing important roles in intracellular transport and tumor cell invasion.

However, in three classical Rho GTPase family members, studies of Cdc42 lag far behind the RhoA and Rac1. This is partly due to fast activation/inactivation cycles of Cdc42, but also to the lack of selective small molecule research tools to help understand this process directly.

The Rho GTPase family proteins are involved in the signaling pathways that regulate a variety of biochemical and cellular functions, e. g. cell membrane and material transport, cell cycle regulation and cytoskeletal organization which is related to the control of cell morphology, cell motility and cell fate. In recent years, studies have shown that deregulated Rho GTPase signaling is involved in the pathogenesis of many diseases, and therefore it has become an important target for drug development.

Applications of small molecule modulators also contributed to the study of the functions of Rho GTPase family proteins. For example, the new types of effective small molecule compounds towards brain and cardiovascular system, fasudil and Y27632, target RhoA downstream effector signaling molecules and are recognized potent Rho/p160$^{ROCK}$ inhibitors. As a Rac1-selective inhibitor, NSC23766 in the recent study of the small molecule compounds targeting Rac1-GEF also greatly facilitate the understanding of Rac1 protein function. However there were almost no effective Cdc42 selective inhibitors. Secramine analogues of natural products galantamine recently showed to behave like a RhoGDI and inhibited Cdc42-dependent Golgi-mediated protein transport through cell membranes. Unlike the widely used Y27632 and NSC23766, the secramine study has been very limited. Cdc42 alteration is closely involved in tumorigenesis in many ways, including tumor transformation and metastasis: in addition, the development and maintenance of neurons is also heavily dependent on the normal Cdc42 activity.

NSC23766 was identified through a computer simulation of the structure of the compounds screened, and it fits the Rac1 molecular surface structure and the known Rac1 essential binding GEF (Cao, Y., J B Dickerson et al (2004) Rational design and characterization of a Rac GTPase-specific small molecule inhibitor. Proc Natl Acad Sci USA. 101 (20): 7618-7623). NSC23766 can inhibit serum or growth factor-induced Rac1 activation and Rac1 mediated lamellipodia formation. NSC23766 inhibits cell proliferation in human prostate cancer cell lines and tumor growth, and reduces cell invasion phenotype of the tumor cells which are dependent on the activity of endogenous Rac1. In addition, new research shows that NSC23766 treatment can improve Rac1-mediated spinal cord injury (SCI)-induced neuropathic pain (Tan, A M, S. Stamboulian, et al (2008). Neuropathic pain memory is maintained by Rac1-regulated dendritic spine remodeling after spinal cord injury. J Neurosci. 28 (49): 13173-13183).

Thus, there is a need to develop inhibitors of Cdc42.

BRIEF DESCRIPTION OF THE DRAWINGS

FIGS. 1A-1C show characterization of described compounds according to one embodiment, and referred to as ZCL compounds, in targeting Cdc42-intersectin (ITSN) interaction: FIG. 1A shows docked pose of ZCL278 in the Cdc42 binding pocket with protein shown as gray surface (Arrow 1) and ligand is shown as sticks (Arrow 2); FIG. 1B shows proposed interactions between ZCL278 and Cdc42 residues, with ZCL278 shown as sticks (Arrow 3), Cdc42 is shown as gray cartoon, residues of Cdc42 are shown as sticks (Arrow 4), and hydrogen bonds are represented as dashed lines (Arrow 5); and FIG. 1C shows superposition of GMP-PCP (Protein DataBank ID code 2QRZ) and the docked Cdc42-ZCL278 complex, with Cdc42 indicated by gray cartoon, ZCL278 by sticks, and GMP-PCP (GMP-PCP is GTP analogs, beta, gamma-methylene diphosphate guanylate) by sticks, as indicated.

FIGS. 2A-2C show properties of ZCL278: FIG. 2A shows the inhibition of Cdc42-mediated cell microspike formation; FIG. 2B shows ZCL278 inhibits the activation of endogenous Rac/Cdc42; and FIG. 2C shows ZCL278 inhibits the stimulated Cdc42 activation.

DETAILED DESCRIPTION

Figure 3A:
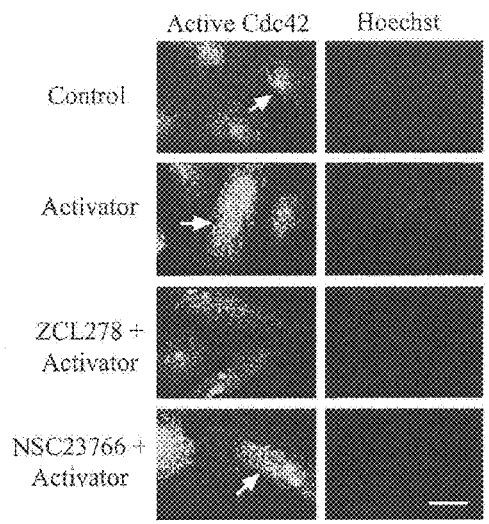
FIGS. 3A-3C show immunofluorescence staining of active Cdc42 and the phosphorylated RhoA.

In one aspect, compounds which inhibit Cdc42 are provided, in one embodiment, the compound has the following structure A:

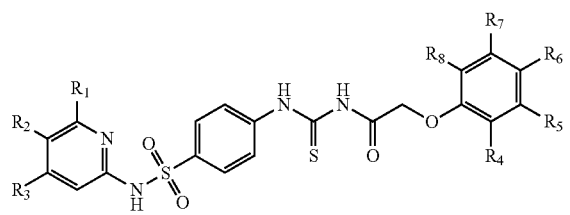

where $R_1$, $R_2$, $R_3$, $R_4$, $R_5$, $R_8$, $R_7$, $R_8$ are each independently selected from the group consisting of fluoro, chloro, bromo, nitro, cyano, amino, methyl, hydroxylmethyl, trifluoromethyl, methoxy, trifluoromethyoxy, and ethyl.

In one embodiment, the compound has the following structure B:

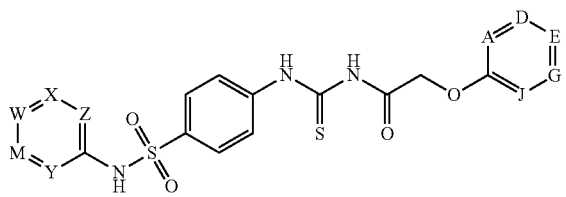

where A, D, E, G, J, M, W, X, Y, Z are each selected from the group consisting of nitrogen, carbon, and substituted carbon, and any of A, D, E, G, J, M, W, X, Y, Z may be missing, such that the ring structure is less than a six-membered ring.

In one embodiment, the compound is a combination of structures A and B. For example, Y and Z are N and $R_1$, $R_2$ and $R_3$, as described for structure A, are attached to X, W, and M of structure B, respectively.

In one embodiment, the compound has the following structure C:

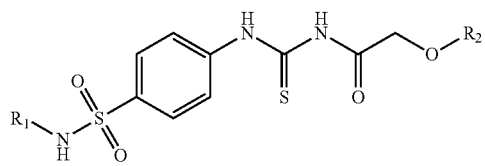

where $R_1$ and $R_2$ are independently selected from the group consisting of alkyl, cyclic alkyl, aryl, and substituted aryl. In one embodiment, $R_1$ is selected from the group consisting of

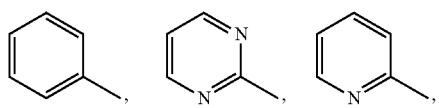

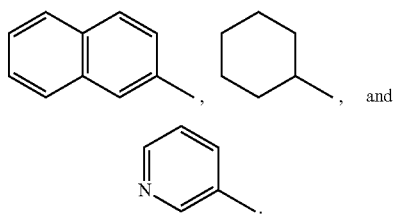

In one embodiment, $R_2$ is selected from the group consisting of

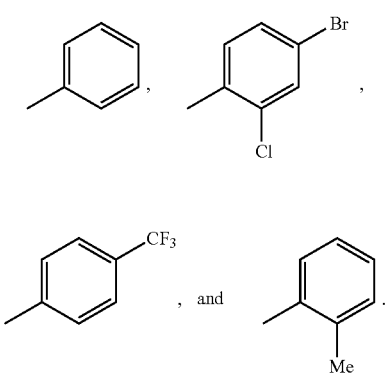

In one embodiment, the compound has the structure of formula I:

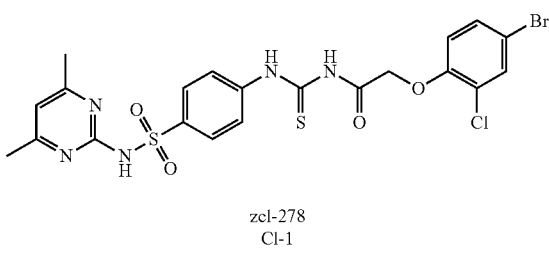

zcl-278
Cl-1

The chemical name of Formula I is 4-(3-(2-(4-Bromo-2-chlorophenoxy)acetyl)thioureido)-N-(4,6-dimethylpyrimidin-2yl)benzenesulfonamide. For the sake of simplicity, it will be referred to as ZCL278 in this application.

In various embodiments, the compound may be a variant of the compound of Formula I selected from the group consisting of Cl-2, Cl-3, Cl-4, and Cl-5, as shown below:

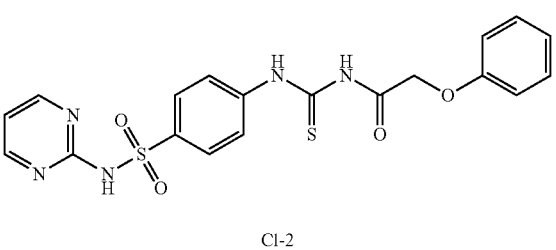

Cl-2

-continued

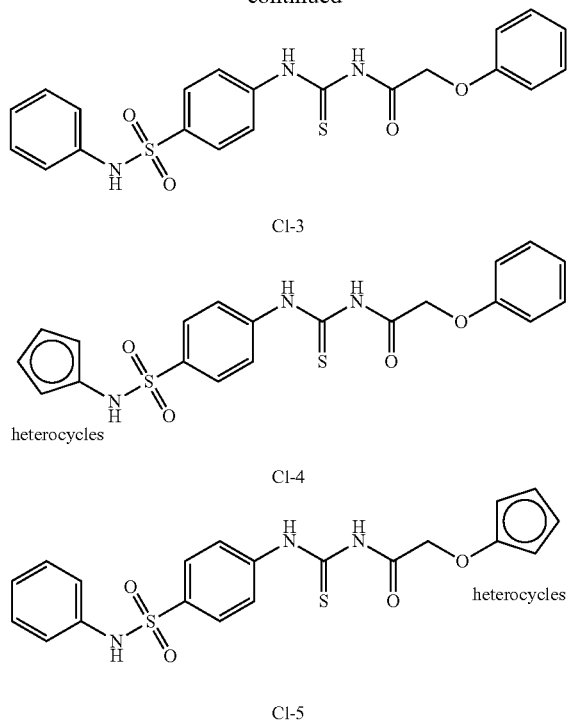

Cl-3 heterocycles

Cl-4 heterocycles

Cl-5

In another aspect, the present compounds, including ZCL278, are used to inhibit Cdc42 and Cdc42 mediated cellular processes. Because Cdc42 has important roles in cell cycle regulation, cell movement, adhesion, apoptosis and intracellular transport, and in the same time it plays important roles in the development of cancer and invasion, cardiovascular system and respiratory diseases, neurological diseases, and many other diseases, the presently described compounds, including ZCL278, can be prepared for the treatment of malignant tumors. In one embodiment, the described compounds may be prepared for the prevention and treatment of malignant tumor development and invasion. In one embodiment, the described compounds can be prepared for the treatment of cardiovascular diseases. In one embodiment, the described compounds can be prepared for the treatment of pulmonary and respiratory diseases. In one embodiment, the described compounds can be prepared for the treatment of diseases of the nervous system. In various embodiments, the described compounds function through inhibition of Cdc42.

As used herein, the term "malignant tumor" is meant to encompass any malignant proliferative cell disorder such as carcinoma, sarcoma, lymphoma and blastoma. Thus, examples of cancers that may be treated using the present method include, but are not limited to, colorectal, prostate, testes, lung, stomach, pancreas, uterine, cervix, bone, spleen, head and neck, brain such as glioblastoma multiforme, breast, ovary, stem cell tumors, non-Hodgkin's lymphoma, Kaposi's sarcoma and leukemia. In the context of the invention, the terms "treat", "treating" or "treatment" means alleviating, inhibiting the progression of, or preventing the cancer, or one or more symptoms thereof.

In one embodiment, the present compound is provided as a pharmaceutical composition. In various embodiments, the pharmaceutical composition may also include one or more pharmaceutically acceptable excipients such as, but not limited to, carriers, diluents, adjuvants and vehicles, Excipients that may be included in the present formulation include preserving or antioxidant agents, fillers, disintegrating agents, wetting agents, emulsifying agents, suspending agents, lubricants such as sodium lauryl sulfate, stabilizers, solvents, dispersion media, tableting agents, colouring and flavouring agents, coatings, antibacterial and antifungal agents, isotonic agents and absorption delaying agents. Supplementary active agents or ingredients may also be included in the present pharmaceutical composition.

ZCL278 effectively suppressed GTP-binding activity of Cdc42. In mouse Swiss 3T3 fibroblasts, ZCL278 affects Cdc42 regulation subcellular structures of two of the most important Cdc42 functions: the elimination of the formation of microspikes or filopodia and disruption of GM130-docked Golgi structures. Compared with Rac-selective inhibitor NSC23766, ZCL278 reduced the peri-nuclear accumulation of active Cdc42. ZCL278 inhibits Cdc42-mediated neuronal branching and growth cone dynamics, and inhibits metastatic prostate cancer cells PC-3 cell actin-based movement and migration without disrupting the cell survival. Thus, because ZCL278 can effectively inhibit Cdc42 regulation of cell morphology and behavior, the compound can play an important role in modulating the development and invasion of cancer, cardiovascular system and respiratory diseases, and nervous system diseases.

The above-mentioned, as well as other related features and advantages, are further provided by the following examples.

Example 1: Virtual Screening for Cdc42 Inhibitors

Virtual screening for Cdc42 inhibitors was performed as described in Friesland et al., PNAS 110; 4, 161-1266 (2013), which is incorporated by reference herein in its entirety. Analysis of the three-dimensional structure of Cdc42-ITSN (intersectin) complex revealed a main binding region between Cdc42 and ITSN. Hydrogen bonds were observed between Gln1380 and Arg1384 of ITSN as well as between Asn39 and Phe37 of Cdc42. Two clusters of hydrophobic interactions were found between Leu1376, Met1379, and Thr1383 of ITSN and Phe56, Tyr64, Leu67, and Leu70 of Cdc42. To screen for Cdc42 inhibitors, the putative binding pocket on Cdc42 was created within 7 Å of the center of the above ITSN residues that interact with Cdc42. The binding pocket consists of 16 Cdc42 residues, including Thr35, Val36, Asn39, Phe56, and Asp57 (FIGS. 1A-1C).

Glide program was applied to screen from SPECS database to identify small molecules that can disrupt Cdc42-ITSN interaction. The structure pose of Cdc42-ITSN complex was from the protein databank (PDB: 1KI1). The ITSN residues that occupy the Cdc42 binding interface are Leu1376, Met1379, Gln1380, Thr1383, and Arg1384. The binding pocket on Cdc42 was created with residues of Cdc42 within 7.0 Å of the center of the above five ITSN residues. After the protein structure was prepared in Protein Preparation Wizard, the docking grid was generated in the Receptor Grid Generation module. The 197,000 compounds from SPECS were screened using HTVS (high-throughput virtual screening) and SP (standard precision) docking sequentially. From the top ranked 50,000 molecules, more stringent SP (standard precision) docking resulted in the top ranked 100 molecules. The top ranked 100 molecules were subjected to manual inspection according to the following criteria. ITSN-like binding posture and occupation for the Leu1376, Gln1380, Arg1384, Met1379, and Thr1383 residue space of ITSN should be observed; at least three hydrogen bonds should be formed; a conserved hydrogen bond with Asn39 or Phe37 Cdc42 should exist, and diversity of scaffolds should be considered. A selection of 30 compounds was eventually tested on their ability to disrupt Cdc42 activity and/or functions.

Computed binding mode of ZCL278 in Cdc42: as shown in FIG. 1A, one small molecule, termed ZCL278, bound to a well-formed Cdc42 pocket lined by residues Thr35, Val36, Asp38, Asn39, Phe56, Tyr64, Leu67, and Leu70. Extensive favorable interactions were found between ZCL278 and Cdc42 residues. Five hydrogen bonds involving residues Thr35, Asn39, and Asp57, as well as hydrophobic interactions associated with residues Val36 and Phe56 were observed (FIG. 1B). The bromophenyl ring was inserted into the adjacent GTP/GDP binding pocket. The computed binding mode suggests that ZCL278 should be able to disrupt the Cdc42-ITSN interaction as well as GTP/GDP binding (FIG. 1C).

Example 2: Synthesis of Compound ZCL278

ZCL278 was synthesized by the following synthetic method. This route of synthesis method is used for illustration, rather than limiting the present invention. Those skilled in the art can understand and expect other synthetic methods to synthesize ZCL278, which also belong to the scope of protection of the present invention.

Reaction Reagents and Conditions: (a) K₂CO₃, DMF (N,N-dimethyl formamide), 70° C.; (b) NaOH, dioxane (dioxane. Embankments B)/H₂O; (c) SOCl₂ (thionyl chloride), DMF, reflux (reflux); (d) NaSCN (sodium thiocyanate), acetone (acetone), 0 C.-room temperature; (e) 4-amino-N-(4,6-dimethylpyrimidin-2-yl)benzene-sulfonamide (4-amino-N-(4,6-dimethyl-2-pyrimidinyl)benzenesulfonamide), 0° C.-room temperature.
The reaction is as follows:

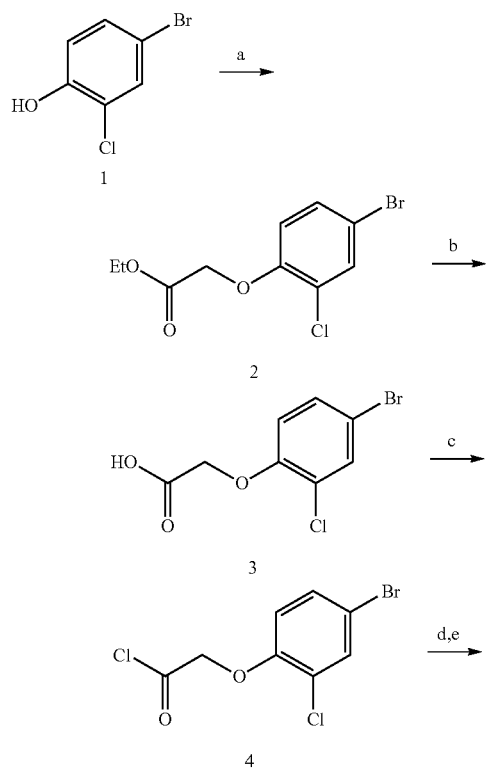

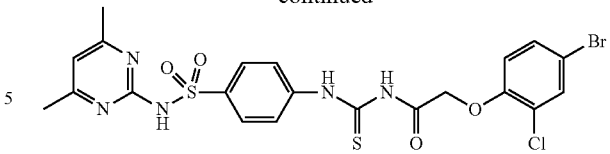

Compound 1 (4-bromo-2-chlorophenol) and 2-ethyl bromoacetate in the presence of K₂CO₃ occur under affinity substitution reaction to give compound 2 (2-(4-bromo-2-chlorophenoxy)acetate). Compound 2 is hydrolyzed under alkaline conditions to give Compound 3 (2-(4-bromo-2-chlorophenoxy)acetic acid). Compound 3 in v, v-dimethylformamide catalyst under reflux to give compound 4 can be prepared in Thionyl. To form the corresponding isothiocyanate intermediate compound 4 (2-(4-bromo-2-chlorophenoxy)acetyl chloride) with sodium thiocyanate, further steps in the reaction system was addition 4-amino-N-(4,6-dimethyl-2-pyrimidinyl) benzenesulfonamide to give compound 5 (i.e., ZCL278).

Instruments and Reagents: Bruker Avance III 400 MHz NMR spectrometer; SGWX-4 melting point apparatus; Agilent 1200-High Performance Liquid Chromatography; ZORBAX Eclipse XDB-C18 Chromatography column (4.6 mm 150 mm, 5 μM); All reagents were of analytical grade or chemically pure.

Step 1: 2-(4-bromo-2-chlorophenoxy) acetate (i.e. Compound 2) Synthesis. Anhydrous K₂CO₃ (3.45 g, 25.0 mM) was added to a solution of 4-bromo-2-chlorophenol (1) (5.2 g, 25.0 mM) and ethyl 2-bromoacetate (4.3 g, 25.7 mM) in 50 DMF. After stirring overnight at 70° C., the mixture was poured into 150 mL water and extracted with ethyl acetate (70 ml×4). The organic layer was combined, washed with brine (100 mL×3), and dried over anhydrous Na₂SO₄. The residue after rotary evaporation was purified by column chromatography to give 2 (6.18 g, 84.1% yield) as a light oil. ¹H NMR (400 MHz, CDCl₃): 7.53 (s, 1H), 7.30 (d, 1H, J=8.4 Hz), 6.72 (d, 1H, J=8.4 Hz), 4.68 (s, 2H), 4.26 (q, 2H, J=7.2 Hz) and 1.29 (t, 3H, J=7.2 Hz).

Step 2: 2-(4-bromo-2-chlorophenoxy) acetic acid (Compound 3) Synthesis. 1 M NaOH (50 mL) was added to a solution of 2 (5.0 g, 17.0 mM) in 50 mL dioxane. After stirring at room temperature overnight, the mixture was acidified with 1 M hydrochloric acid to pH=3. After the reaction mixture was extracted with ethyl acetate (50 mL×4), the organic layer was washed with brine (50 mL), dried over anhydrous Na₂SO₄, and concentrated to give 3 (4.69 g, 94.3% yield) as a white solid. ¹H NMR (400 MHz, DMSO-d6): 7.66 (s, 1H), 7.44 (d, 1H, J=8.8 Hz), 6.97 (d, 1H, J=8.8 Hz), 4.72 (s, 2H).

Step 3: Preparation of 4-(3-(2-(4-bromo-2-chlorophenoxy)acetyl)thioureido)-N-(4,6-dimethyl-2-pyrimidinyl) benzene—Synthesis of the sulfonamide (i.e., compound 5). Compound 3 (539 mg, 2.0 mM) in 25 mL SOCl₂ and a drop of DMF were heated to reflux. After 3 hours, SOCl₂ was removed by distillation and the residue was dried in vacuo for 5 minutes to give crude acyl chloride 4. The solution of 4 in 10 mL dry acetone was added drop-wise into sodium thiocyanate (326.8 mg, 4.0 mM) in 10 mL acetone at 0° C. The mixture was stirred at 30° C. for 2 hours before 4-amino-N-(4,6-dimethyl-2-pyrimidinyl) benzenesulfonamide (556 mg, 2.0 mM) was added at 0° C. After stirring at temperature overnight, the mixture was filtered and washed with water and acetone to give compound 5 (276 mg, 23.6% yield) as a yellow powder. ¹H NMR (400 MHz, DMSO-d6):

12.19 (s, 1H), 11.68 (s, 1H), 11.52 (br s, 1H), 7.99 (d, 2H, J=8.4 Hz), 7.86 (d, 2H, J=8.4 Hz), 7.70 (d, 1H J=1.6 Hz), 7.49 (d, 1H, J=8.8 Hz), 7.10 (d, 1H, $J_1$=8.8 Hz, $J_2$=1.6 Hz), 6.75 (s, 1H), 5.02 (s, 2H), 2.25 (s, 6H), HPLC: purity 95.9% (254 nm).

Example 3: Direct Binding of ZCL278 and Cdc42 Demonstrated by Fluorescence Titration and Surface Plasmon Resonance The binding affinity of ZCL278 and Cdc42 was assessed by using two independent biophysical methods. First, fluorescence titration of purified Cdc42 ZCL278 was carded out by monitoring the change of fluorescence intensity of a tryptophan residue on CAc42 upon ZCL278 binding. As ZCL278 has a weak absorption peak at 310 nm, to avoid any experimental error that might result from potential fluorescence quenching by ZCL278, the fluorescence emission of Cdc42 was monitored at 350 nm, at which ZCL278 has a negligible absorption. Thus, a Kd value of 6.4 μM was obtained. To further demonstrate the direct interaction between ZCL278 and Cdc42, a surface plasmon resonance (SPR) experiment was performed by covalently immobilizing purified Cdc42 onto CM5 chips and varying ZCL278 concentration. The SPR response was observed to increase along with elevated ZCL278 concentrations, and eventually gave a Kd 11.4 μM. To support the Kd measured in our system, the solubility of ZCL278 was determined to be 181 μM and was greater than the concentrations used in examples. The experimental pKa values of ZCL278 were determined to be 3.48±0.04, 6.61±0.02, and 7.45±0.01. The pKa value of 3.48 is associated to pyrimidine nitrogen that should stay in a neutral form at pH 7.4 The NH groups corresponding to pKa values of 6.61 and 7.45 should be partially deprotonated and give a population of charged species in solution. These species in solution may have modifying effects on membrane transport and binding to Cdc42.

Example 4: Activity Characteristic of the Embodiment of ZCL278

1. ZCL278 Inhibits Cdc42-Mediated Microspike Formation.

30 selected ZCL compounds were assessed for their ability to inhibit Cdc42-mediated microspike/filopodia formation in serum-starved Swiss 3T3 fibroblasts. Actin-based microspikes/filopodia are characteristic of Cdc42 activity in cultured fibroblastic cells. As shown in FIG. 2A, DMSO-treated (control) cells have few microspikes along its perimeter (Arrows) as well as the characteristic presence of RhoA-mediated stress fibers (Asterisk). When arrested fibroblasts were briefly stimulated with 1 unit/mL of a commercial Cdc42 activator, a dramatic increase in microspike number and decrease in stress fibers occurred (FIG. 2A, Activator). Compound ZCL278 was applied at 50 μM for 1 hour and then stimulated with the Cdc42 activator for 2 minute. The cell periphery of ZCL278-treated cells resembles control cells with few microspikes (FIG. 2A, ZCL278). Following 1 hour of ZCL278 treatment and Cdc42 stimulation; there is obvious inhibition of microspike formation (FIG. 2A, Activator+ZCL278) as compared to cells treated with only the activator (FIG. 2A, Activator).

2. ZCL278 Inhibits Cdc42 activity.

Since ZCL278 showed the direct binding to Cdc42 and displayed most inhibitory effects in a morphological assay of Cdc42 function, the activity of the compound was examined at a biochemical level. First, Cdc42 activation was investigated in human metastatic prostate cancer PC-3 cells that were treated with the Cdc42 activator or 50 μM ZCL278 for 5, 10, and 15 minutes. Serine 71 phosphorylation is known to negatively regulate Rac/Cdc42 activity, thus an increase: in phospho-Rac/Cdc42 expression is indicative of a decrease in active (GTP-bound) Rac/Cdc42. As depicted in FIG. 2B, activation of Cdc42 shows an expected decrease in phospho-Rac/Cdc42. However, the application of ZCL278 resulted in a time-dependent increase in Rac/Cdc42 phosphoryiation.

Wiskott-Aldrich syndrome Protein WASP) is a downstream effector of Cdc42 activation. Tyrosine phosphorylation WASP is linked to rapid Cdc42 degradation following its activation. As shown in FIG. 2B, the Cdc42 activator leads to a decreased expression of phospho-WASP by 15 minutes while ZCL278 does not suppress phospho-WASP activity. Thus, ZCL278 inhibits Rac/Cdc42 phosphorylation in a time-dependent manner and maintains tyrosine phosphorylation of WASP.

Serine 71 phosphorylation can occur on both Rac and Cdc42. To directly assess specific Cdc42 activation and inactivation, a G-LISA, an ELISA-based assay that allows a quantitative determination of the levels of GTP-bound (active) Cdc42 in cellular lysates was utilized. Serum-starved Swiss 3T3 fibroblasts were incubated for 1 hour with 50 μM ZCL278 or 10 μM NSC23766 (Rac inhibitor), followed by 2 minutes of stimulation with 1 unit/mL Cdc42 activator. This analysis revealed a significant increase (70%) in GTP-bound Cdc42 in cells treated with the activator as compared to control (untreated) cells (FIG. 2C). Cells treated with ZCL278 showed a dramatic (nearly 80%) decrease in GTP-Cdc42 content as compared with cells treated solely with the activator.

Finally, the ability of NSC23766 to cross-inhibit Cdc42 activation was analyzed. NSC23766 was developed in a similar manner as ZCL278; however, it is specific to Rac and should therefore act as an additional negative control in this assay. As expected, NSC23766 does not reduce GTP-Cdc42 content (FIG. 2C). These data establish that ZCL278 inhibits Cdc42 in two different cell types.

Example 5: The Immunofluorescence Staining of Active Cdc42/Phosphorylated RhoA

1. ZCL278, Rather Than NSC23766, Disrupts Perinuclear Distribution of Active Cdc42.

Immunofluorescent staining: Swiss3T3 cells were grown on coverslips to 30% confluence. In serum-deprived culture, cells were treated with 10 uM NSC23766 or 50 uM ZCL278 for 1 hour followed by 1 unit/mL Cdc42 agonists (Cytoskeleton Products) treatment for 1 minute. Added agonist alone was used as a positive control while DMSO was used as a negative control. Cells on the coverslips were fixed in 4% paraformaldehyde for 15 minutes, and in 0.2% Triton X-100 for permeabilization for 15 minutes and then blocked in 10% BSA for 30 minutes.

Incubation with antibodies: anti-active Cdc42 (mouse antibody, Neweast Biosciences); phosphorylated RhoA antibody (rabbit antibody, Santa Cruz Biotechnology Company); GM130 antibody (mouse antibody, BD Biosciences Company). The next step was to apply corresponding secondary antibody. Rhodamine, Phalloidin was incubated for 1 hour at room temperature to observe filamentous actin under the Zeiss Axiovert fluorescent light microscopy of cells staining. Image processing software MetaMorph-5 was used to randomly select cells in randomly selected five-point pixels to obtain the average number of each group for pixel intensity values.

The Western blot: PC3 cells cultured to approximately 70% of the density, then removed serum and cultured for 16 hours, with addition of drugs: 1 unit/mL Cdc42 agonist (cytoskeleton) 5 uM, 50 uM ZCL278 to treat cells for 5, 10, and 15 minutes respectively. Cell lysis buffer (Formulation: 50 mM Tris buffer solution pH 7.5, 10 mM magnesium chloride, 0.5 M sodium chloride, 1% Triton X-100 and protease inhibitors) cell lysis and centrifuged at 14000 rpm and 4° C. to obtain extracted protein samples. Western blot analysis was conducted using antibody: phosphorylated Rac1/Cdc42 (Milipore Company), phosphorylated WASP (Assay Biotech Company), all at 1:1000, and GAPDH antibody (Calbiochem Company) on PVDF membrane for chemiluminescence development.

G-LiSA kit: Swiss 3T3 cells were cultured to 40% of the growth density, then removed serum and cultured for 48 hours, treated with Cdc42 agonist for 1 minute, and treated with the 50 uM ZCL278 and 10 uM NSC23766. Cell lysis proteins were extracted according to kit instructions, and analysis of the quantification of total protein concentration to be 0.15 mg/ml. Untreated cells or cells treated with buffer were used as negative control while the agonist treated cells and active Cdc42 protein were used as a positive control. Enzyme linked immunosorbent assay measured the absorbance value of each sample 490 nm light wave.

Figure 3B:
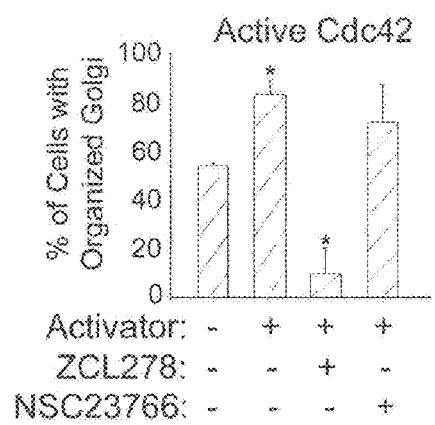
Figure 3C:
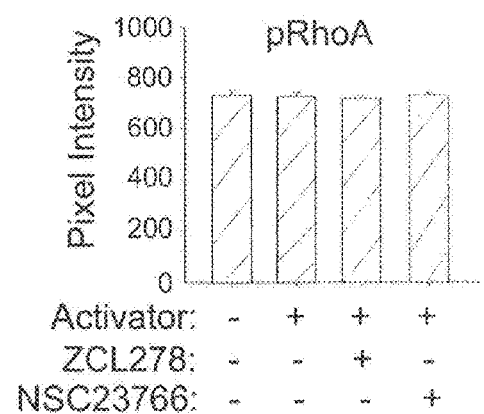

Determination of selective inhibition of Cdc42 activation by ZCL278 at the cellular level. Serum starved Swiss3T3 cells were treated with 1 unit/ml Cdc42 agonist for 2 minutes, then treated with 50 uM ZCL278 or NSC23766 10 uM, while DMSO to be used as a negative control. To determine the role of ZCL278 to selectively inhibit Cdc42 activity rather than the role of RhoA, cells were immunostained with anti-active Cdc42 (FIG. 3A, FIG. 3B) and phosphorylated RhoA (FIG. 3C): Arrow: perinuclear Golgi-endoplasmic reticulum network; Hoechst staining identifies the nucleus. Bar: 15 um. As shown in FIG. 3A, immunofluorescence staining: mouse monoclonal antibody against active Cdc42, and Hoechst (identified nucleus). While control group cells showed activation of Cdc42 in the nucleus and perinuclear organization, agonists significantly increased its distribution and distribution in the nucleus, which is consistent with the role of Cdc42 involved in Golgi protein transport. ZCL278 obviously reduced this distribution, and reduce immunoreactivity to active Cdc42. NSC23766 did not have similar effects. FIG. 3B shows the number of cells of each group with Golgi-like distribution, randomly selected 6 cells were independently counted for Golgi-endoplasmic reticulum network (*:p<0.05). FIG. 3C: Pixel intensity of phospho-RhoA in cells after treatments with Activator, ZCL278, or NSC23766 was quantified. Results reflect the averaged intensity generated at five random points in five independent cells (n=5/group)±S.E. (*.p<0.03). Agonists, ZCL278, and NSC23766 did not alter the phosphorylation RhoA. This result suggests that ZCL278 selective inhibits Cdc42 activity.

2. ZCL278, but not NSC23766, Disrupts GM130 Docked Golgi Organization.

To determine whether the ZCL278-induced disruption of peri-nuclear distribution of active Cdc42 reflected its effects on Golgi organization, GM130, a peripheral cytoplasmic protein that is tightly bound to Golgi membranes and helps to maintain cis-Golgi structures, was examined.

Figure 4:
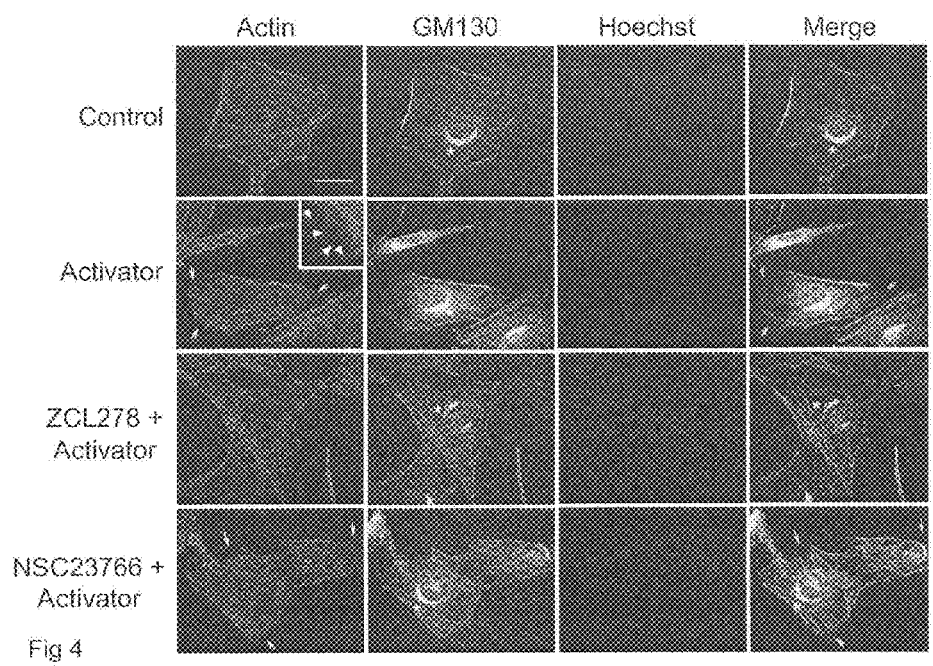
FIG. 4 shows ZCL278 disrupts the GM130-docked Golgi organization.

Control, serum-starved Swiss 3T3 cells showed well-developed stress fibers (FIG. 4, Red) and GM130 immunoreactivity polarizing to one side of the nucleus (FIG. 4, Green-asterisk). Treatment with the Cdc42 activator led to increased microspikes, as expected (FIG. 4, Red-arrows and insert, arrowheads), and intense peri-nuclear GM130 immunoreactivity (FIG. 4, Green-asterisk). As depicted in FIG. 4 (also see FIG. 2A), ZCL278-treated cells showed not only fewer microspikes but also a clear reduction of GM130 immunoreactivity as well as its dissipation to both skies of the nucleus (FIG. 4, Green-asterisk). Rac inhibitor NSC23766 did not significantly after GM130 expression or distribution (FIG. 4—Green-asterisk). These results not only further confirm ZCL278 as a specific Cdc42 inhibitor, but also demonstrate the importance of Cdc42 Golgi organization and protein trafficking.

Example 6: ZCL278 Impedes Wound Healing without Disruption of Cell Viability

Filopodia are dynamic structures that aid cells in pathfinding and migration, and are largely controlled by Cdc42 activity. Using a metastatic line of human prostate cancer cells (PC-3), a wound healing assay was used in order to elucidate the effects of ZCL278 on cellular migration. 1 unit/ml Cdc42 activator; 50 uM or 5 uM of ZCL278; and 10 uM NSC23765 respectively, were used to treat cells for 24 hours, with Cdc42 activator as positive control, and no treatment as negative control. Cells were photographed at 0 and 24 hours following drug treatments and MetaMorph software was used to determine the distances cells had migrated. Black line indicates the boundary of wounded area. Each experiment was tested with p value (p<0.05).

Examination of cell survival: PC3 cells were plated at 75000/ml for 48 hours, serum was removed and 50 uM ZCL278 or 10 uM NSC23766 was added, and then continue to culture for 24 hours before staining with trypan blue to determine cell survival rate.

Figure 5A:
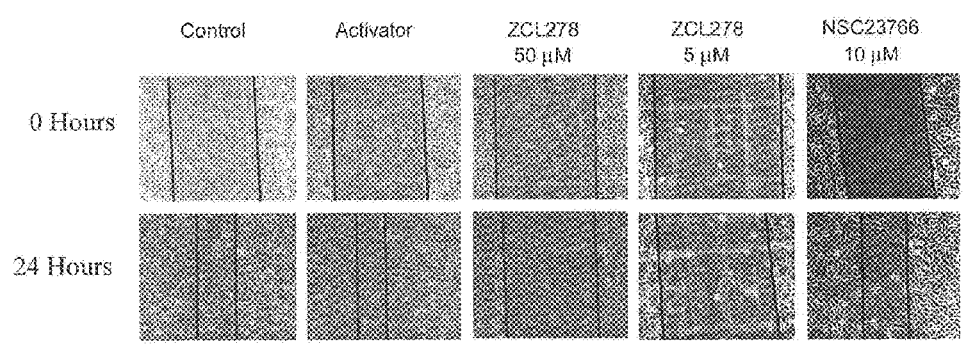
FIGS. 5A-5C show ZCL278 suppresses cell migration without affecting cell viability.
Figures 5B, 5C:
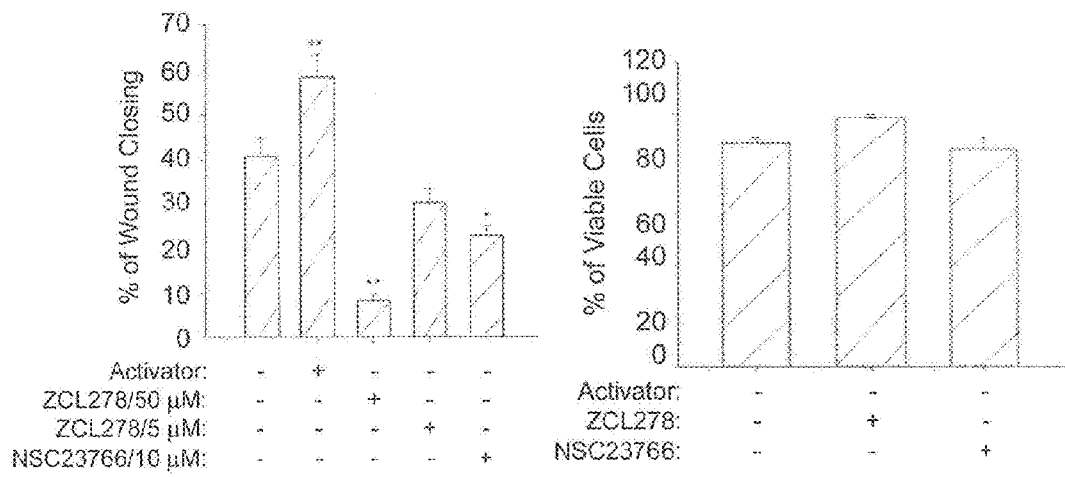

As shown in FIG. 5A and quantified in FIG. 5B, Cdc42 activation resulted in a significant increase (59%) in wound healing ability in comparison to controls (41%). Bar graph shows the wound area compared to that before drug treatment. The experiment was repeated three times and the means were obtained:**; p<0.01,*:p<0.05. Wound closure was less pronounced at 50 μM (8%) than 5 μM (30%) concentrations. Cellular migration was also significantly reduced with NSC23766 treatment. This result is to be expected since Rac regulates the formation of lamellipodia, which are well-described motile structures. These data, which are in agreement with our biochemical analysis, suggests that ZCL278 is not only a selective inhibitor of Cdc42 activation but also a potent suppressor of Cdc42-dependent cell motility.

In order to ensure that decreases in cellular migration seen with ZCL278 treatment was due to Cdc42 inhibition (or Rae inhibition when treated with NSC23766) rather than cell death, cell viability was tested using the trypan blue dye exclusion assay. PC-3 cells were arrested in G0, and then 50 μM ZCL278 or 10 μM NSC23766 was applied for 24 hours. FIG. 5C demonstrates that there was no difference in viability between treated and non-treated (control) cells. Therefore, the differences seen in migratory ability is due to ZCL278-mediated Cdc42 inhibition or NSC23766-mediated Rac inhibition and not cell death.

Example 7: ZCL278 Inhibits Neuronal Branching and Growth Cone Dynamics

Cdc42 plays a crucial role in the establishment of neuronal morphogenesis Cdc42's absence in neurons results in a significantly reduced number of neurites and severely disrupted filopodia function. Therefore, the ability of ZCL278 to inhibit neuronal branching in primary neonatal cortical neurons was tested.

Primary neonatal day-one mouse brain was incubated with 0.25% trypsin HBSS for 15 minutes at 37° C., gently separated neurons were plated on poly-L-lysine coated coverslips, incubated with DMEM containing 10% bovine serum for 16 hours, then the media was changed to Neurobasal (Invitrogen). At 5 days in vitro, the cells were treated with either DMSO or 50 uM ZCL278 for 5 or 10 minutes, then fixed in 4% paraformaldehyde for 15 minutes. Fluorescein-phalloidin was applied to stain for F-actin structure and the neuronal morphology was observed under the Zeiss light microscope.

Figures 6A, 6B:
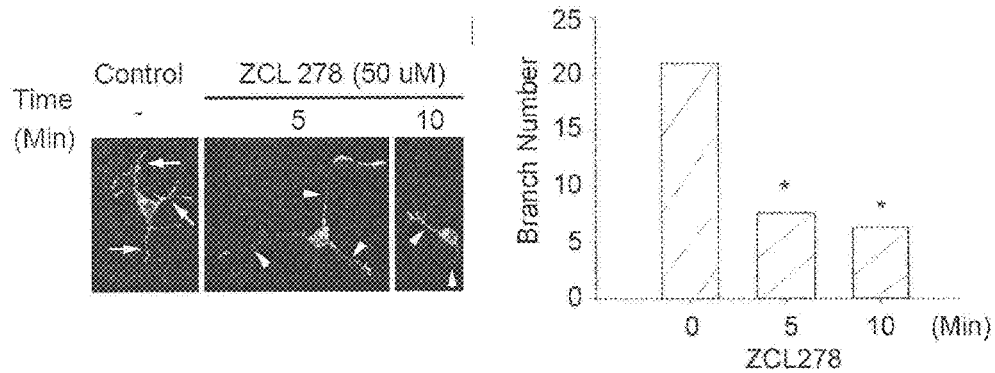
FIGS. 6A-6C show ZCL278 inhibits neuronal branching and growth cone dynamics.

Time-lapsed video light microscopy was used to observe the effects of ZCL278 on neuronal growth cone dynamics, Hamamatsu Orca digital camera was used to record the cell images under 63× magnification for 10 minute. 300 ms exposure for imaging was used to minimize phototoxicity. The images were analyzed using MetaMorph software and statistical analysis was performed. At 5 days cultured in vitro, cortical neurons extended neurites with multiple branches (FIG. 6A, Control). 50 μM of ZCL278 was applied for 5 and 10 minutes, while DMSO-treated neurons were maintained as negative controls. As demonstrated in FIG. 6A, neuronal branching was suppressed in ZCL278-treated neurons over the time course in comparison to the highly branched neurites of control cells. Quantitative measurements found the branch number to be significantly reduced in ZCL278 treated neurons (FIG. 6B: Quantitation of neuronal branching number following ZCL278 treatment: The data represent the means after three independent experiments±standard errors, *:p<0.01).

Figure 6C:
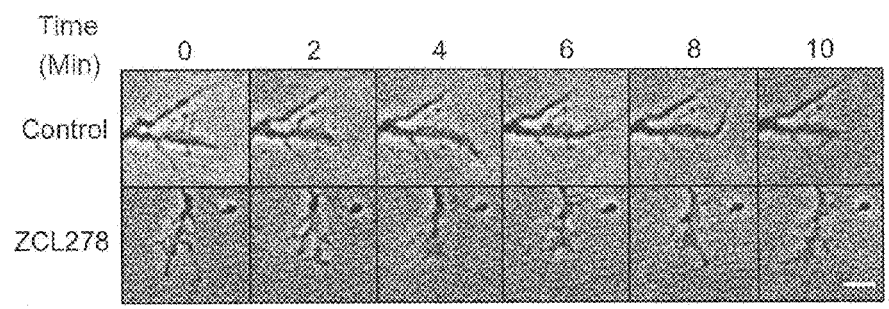

Cdc42 is also widely known to control filopodia and microspikes at the leading edge of migrating growth cones. Time-lapse video light microscopy shows a control cortical neuron with multiple microspikes or filopodia extended from the growth cone (FIG. 6C). However, ZCL278 treatments resulted in rapid retraction of filopodia within 4 minutes (FIG. 6C). Thus, these studies further support ZCL278 as an effective small-molecule inhibitor of Cdc42-mediated neuronal branching and growth cone motility.

The present description provided computer simulation methods which were applied for high-throughput in silico screening of compounds that target chimeric Cdc42-GEF structures. Based on the structure characteristics of Cdc42 and its specific GEF intersectin (ITSN), the three-dimensional structure of the described compounds can fit exactly into the pocket that intersectin interacts with Cdc42. Additional research successfully screened and identified a compound ZCL278 as a cell permeable Cdc42 specific inhibitor.

The present description confirmed the active properties of ZCL278 as the first small molecule inhibitor Cdc42, selectively targeting Cdc42 and its GEF intersectin. Cell wound healing experiments showed that activated Cdc42 promotes the wound closure and tumor cell metastasis. ZCL278 significantly inhibits the migration of PC3 cells in a concentration-dependent manner. ZCL278 inhibits cell migration but it is not cytotoxic and does not cause cell death.

Also, the neonatal central neurons experiments have proved that the Cdc42 plays an important role in the development of neurons. Garalov et al. (J. Neurosci. 27(48): 13117-13129) showed that Cdc42-deficient mice exhibited brain and neuronal development which was severely disrupted. These mice showed a series of brain malformations, including the reduction of the axon bundles, as well as neurons filamentous pseudopodia dynamics and reduced growth cone, and suppression of axonal extension. In fact, the movement of axons and dendrites is mainly actin-based, the process also regulated by Cdc42. ZCL278 can reduce the number of branches of the newborn central neurons, and inhibition of the growth cone dynamics. In summary, ZCL278, which targets Cdc42-ITSN, is the first small molecule inhibitor that can be effectively used in the studies of molecular functions of Cdc42 in cancer and neurological disorders.

Although the present invention has been presented with the disclosed embodiments, it is not intended to limit the present invention. A person having ordinary skill in the art, without departing from the spirit and scope of the present invention, will recognize that modifications and improvements of these embodiments are within the scope of the present description.

What is claimed is:

1. A method for inhibiting Cdc42 mediated neuronal branching, the method comprising contacting Cdc42 within a neuron with a composition comprising a compound of formula I:

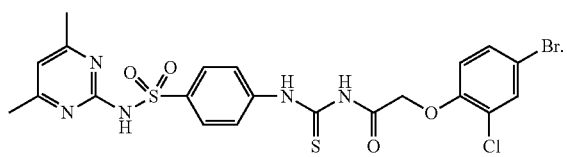 [SMILES: Cc1cc(C)nc(NS(=O)(=O)c2ccc(NC(=S)NC(=O)COc3ccc(Br)cc3Cl)cc2)n1]

2. The method of claim 1 wherein the composition is provided as a pharmaceutical composition comprising the compound of formula I and at least one excipient.

* * * * *